(12) United States Patent  
Stanley

(10) Patent No.: US 11,786,127 B2  
(45) Date of Patent: Oct. 17, 2023

(54) DISPOSABLE THUMB LIGHT

(71) Applicant: Anthony G. Stanley, North Bay Village, FL (US)

(72) Inventor: Anthony G. Stanley, North Bay Village, FL (US)

(73) Assignee: STANLEY MEDICAL DESIGNS, INC., North Bay Village, FL (US)

( * ) Notice: Subject to any disclaimer, the term of this patent is extended or adjusted under 35 U.S.C. 154(b) by 244 days.

(21) Appl. No.: 17/022,211

(22) Filed: Sep. 16, 2020

(65) Prior Publication Data

US 2021/0085183 A1 Mar. 25, 2021

Related U.S. Application Data

(60) Provisional application No. 62/903,126, filed on Sep. 20, 2019.

(51) Int. Cl.
*A61B 5/00* (2006.01)
*F21V 23/04* (2006.01)
(Continued)

(52) U.S. Cl.
CPC ............ *A61B 5/0059* (2013.01); *F21L 4/045* (2013.01); *F21V 23/0492* (2013.01);
(Continued)

(58) Field of Classification Search
CPC ............. F21V 33/0008; F21V 33/0068; F21V 23/0492; A61B 5/0059; A61B 2560/0431; F21L 4/045; F21W 2131/20
See application file for complete search history.

(56) References Cited

U.S. PATENT DOCUMENTS 6,709,142 B2  3/2004  Gyori
7,347,578 B1  3/2008  Nourse
(Continued)

FOREIGN PATENT DOCUMENTS

WO    WO 2010/085958    8/2010

OTHER PUBLICATIONS

Amazon. "Coroler Cool Fingerless LED Flashlight Gloves for Repairing, Working in Darkness Places, Fishing, Camping, Hiking and Outdoor Activities" Amazon.com (2017) pp. 1-2.
(Continued)

*Primary Examiner* — Thomas M Sember
(74) *Attorney, Agent, or Firm* — Dority & Manning, P.A.

(57) ABSTRACT

A disposable thumb light and a method of providing direct lighting for a medical procedure on a patient using a disposable thumb light is described. The disposable thumb light includes a housing, a light source, and at least one attachment configured to couple the disposable thumb light to a thumb of a user or a glove. The housing can include at least one flexible portion. The disposable thumb light can further include a flex responsive switch that is configured to move between at least a first position and a second position when the housing moves from a first housing position to a second housing position and energize or de-energize the light source in response. In the method of providing direct lighting for medical procedure, the disposable thumb light is coupled to a thumb of a user; the light source is energized by moving the thumb of the user from a first position to a second position; and the light source is de-energized by moving the thumb of the user from the second position toward the first position.

7 Claims, 3 Drawing Sheets

(51) Int. Cl.
    *F21V 33/00*     (2006.01)
    *F21L 4/04*     (2006.01)
    *F21W 131/20*     (2006.01)

(52) U.S. Cl.
    CPC ...... *F21V 33/0008* (2013.01); *F21V 33/0068* (2013.01); *A61B 2560/0431* (2013.01); *F21W 2131/20* (2013.01)

(56) References Cited

U.S. PATENT DOCUMENTS

| | | |
|---|---|---|
| 8,747,306 B1 | 6/2014 | Ramos |
| 9,402,582 B1 | 8/2016 | Parviz et al. |
| 10,143,527 B2 | 12/2018 | Schneider et al. |
| 2013/0085325 A1 | 4/2013 | Fuller et al. |
| 2015/0327599 A1 | 11/2015 | Bouza et al. |
| 2017/0086521 A1 | 3/2017 | Sterner |

OTHER PUBLICATIONS

Bean Tech Games. "Fiber Optic Light Glove, Gloves Flashlights" *Bean-TechGames Blog Spot* (2014) pp. 1-2.
Kobakant. "Openwear Finger Bend Sensor" *How to Get What You Want* (2017) pp. 1-6.

DISPOSABLE THUMB LIGHT

CROSS REFERENCE TO RELATED APPLICATION

This application claims filing benefit of U.S. Provisional Patent Application Ser. No. 62/903,126, having a filing date of Sep. 20, 2019, which is incorporated herein by reference for all purposes.

FIELD OF THE INVENTION

The subject matter of the present invention relates generally to a method of providing direct lighting for a medical procedure using a thumb light, e.g., a disposable thumb light, configured to be coupled to a medical practitioner's finger in order to illuminate the field of manipulation during a procedure.

BACKGROUND

Surgeons, doctors, and other healthcare practitioners frequently perform procedures that require good visualization and direct lighting in the vicinity of the practitioner's hand. For instance, surgical wound repair such as suturing, ear lavage, location and removal of foreign objects from narrow or deep body cavities, general physical examination of body cavities and wounds, and eye examinations each require direct visualization with good lighting.

Foreign body removal is a common medical procedure which encompasses the removal of a foreign object from a body cavity, including the ear, nose, eye, vagina, and/or a wound. For instance, to remove a foreign body from the ear, various instruments such as alligator forceps, curettes, plain forceps, right angle hook, balloon catheter, lavage instruments such as a syringe or soft tip suction catheter, among others, may be used. However, visualization of the foreign object by the practitioner is required before the practitioner can determine the best suited removal procedure. Unfortunately, every individual will vary somewhat with regard to, e.g., shape, direction, and length of body parts, e.g., the ear canal, as well as location of adjacent nerves (e.g., the auricular branch of the facial nerve and the auricular branch of the vagus nerve) and other structures that could be damaged or irritated by the procedure. As such, foreign body location and removal procedures can require patience, dexterity, and in many cases, assistance for positioning and manipulation of the body part so as to alternately visualize the area and manipulate the instrument used to remove the foreign object. For instance, it can be necessary to manipulate the outer ear with one hand to modify the shape/location of the ear canal while alternately handling the foreign body removal instrument. Similar issues exist in other foreign body location and removal protocols in which the practitioner is attempting to both see and remove a foreign object in a small, often difficult to visualize area.

In order to successfully locate and remove a foreign object from a body cavity without touching or damaging sensitive body tissues as described above, proper protocols for foreign body removal require direct visualization of the body cavity with good lighting. Often, a secondary lighting source, e.g., an additional lamp, is required to supplement the light of a procedure room. For instance, the practitioner performing the foreign body removal may wear a headlamp or may require additional personnel to hold and/or adjust a floor lamp, a hand-held lamp, or other lighting source. However, these secondary lighting sources may require continual adjustment of the positioning of the lighting source due to shadows, patient movement, movement of the foreign body removal instrument within the body cavity, etc., which can increase the procedural time, thereby increasing patient discomfort. Moreover, none of these secondary lighting sources are guaranteed to directly illuminate the area surrounding the practitioner's hand in order to best visualize and remove the foreign object.

Consequently, there is a need for a light apparatus configured to be coupled to a practitioner's thumb in order to directly illuminate the area surrounding a practitioner's manipulating hand, e.g., thereby directly illuminating the area for a medical procedure. In particular, a disposable light apparatus would also be useful.

SUMMARY

The present invention is directed to a disposable thumb light that includes a housing, a light source, and at least one attachment configured to couple the disposable thumb light to a thumb of a user or a glove. The housing can include at least one flexible portion. The disposable thumb light can further include a power source and a flex responsive switch that is configured to move between at least a first position and a second position when the housing moves from a first housing position to a second housing position and energize or de-energize the light source in response.

The present invention is further directed to a method of providing direct lighting for a medical procedure on a patient utilizing the disposable thumb light. The method of providing direct lighting includes providing the disposable thumb light, coupling the disposable thumb light to a thumb of a user, e.g., on a manipulating hand of the user; energizing the light source by moving the thumb of the user from a first position to a second position, and de-energizing the light source by moving the thumb of the user from the second position toward the first position.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
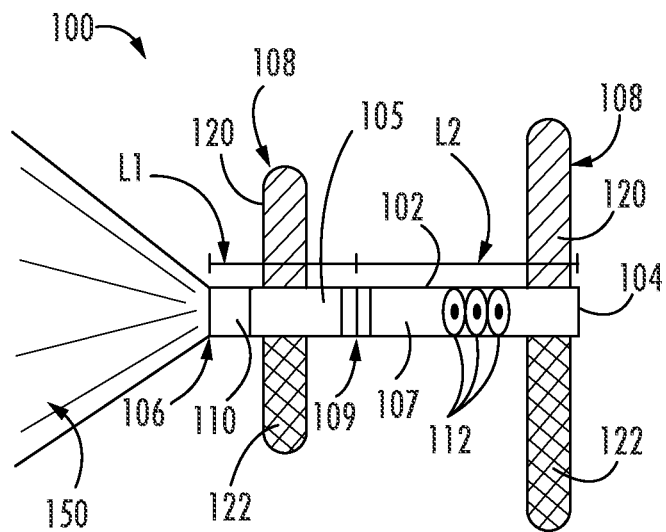
FIG. 1 illustrates a top view of a disposable thumb light according to one particular embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally speaking, the present invention is directed to a disposable thumb light and a method of providing direct lighting for a medical procedure on a patient utilizing the disposable thumb light. The disposable thumb light includes a housing, a light source, and at least one attachment configured to couple the disposable thumb light to a thumb of a user or a glove. The housing can include at least one flexible portion. The disposable thumb light can further include a power source and a flex responsive switch that is configured to move between at least a first position and a second position when the housing moves from a first housing position to a second housing position and energize or de-energize the light source in response. Disclosed devices can provide benefit to the art, such as by preventing accidental trauma and irritation to a patient—as has been known to happen previously—due to an inability to visualize an area clearly during a procedure such as foreign body removal. Disclosed devices can also save time and money for a practitioner, as the single operator use of the device can remove the necessity for a second practitioner to be present to assist with positioning of a light for a procedure. For instance, the practitioner can implement the disposable thumb light of the present invention on a manipulating hand to simultaneously manipulate, e.g., reposition, and illuminate a part or piece, e.g., a patient's body part in the specific embodiment of a medical application, while performing a procedure with the other hand. In addition, disclosed devices may have further applications outside the medical field, e.g., veterinary, military, or other applications. The specific features of the disposable finger light of the present invention may be better understood with reference to FIGS. 1-6.

Figure 2:
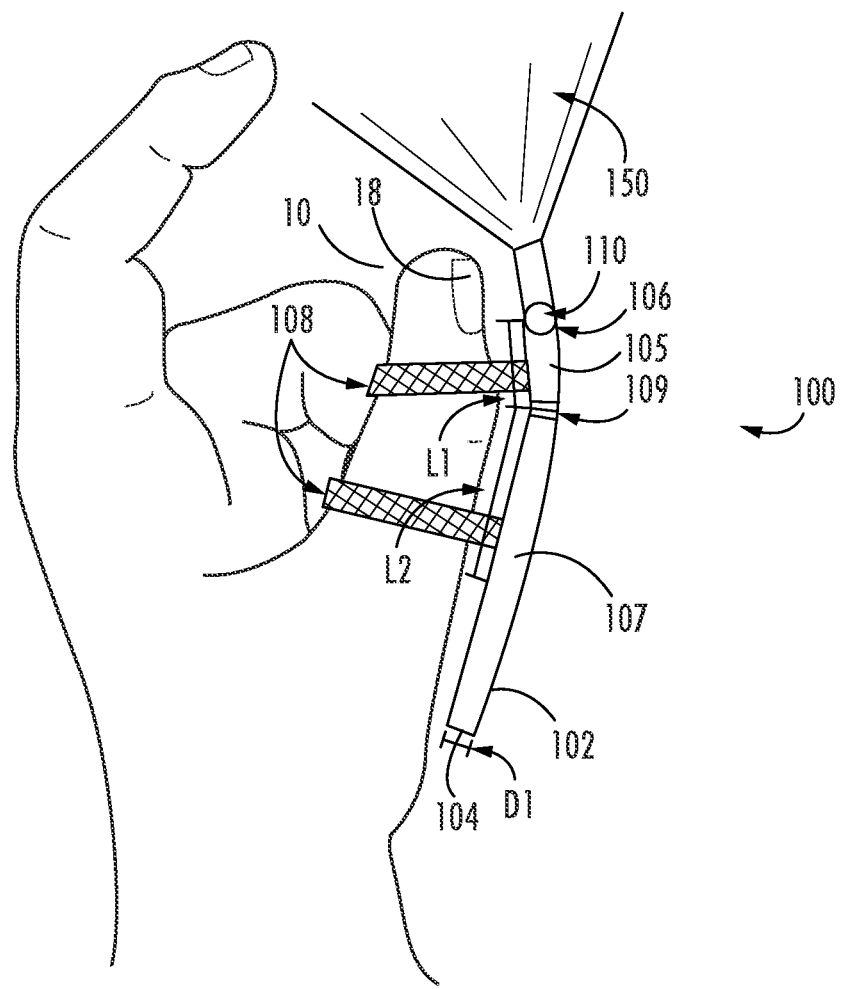
FIG. 2 illustrates a side view of the disposable thumb light of FIG. 1 attached to a finger of a user, in a state in which the light source is energized.
Figure 3:
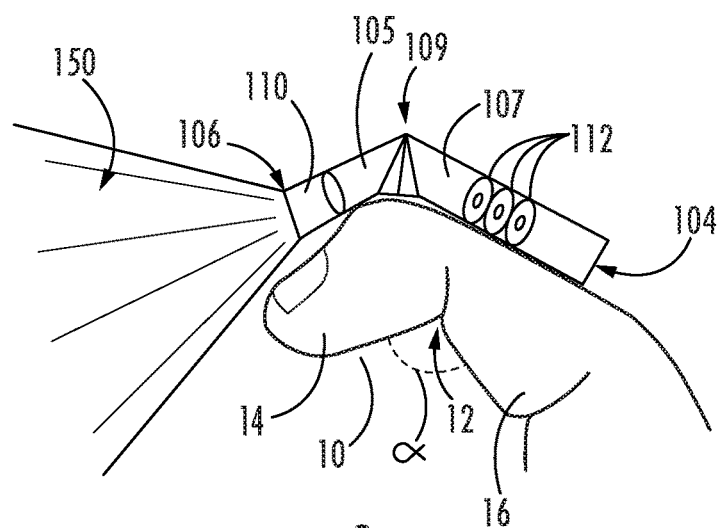
FIG. 3 illustrates a side view of the disposable thumb light of FIG. 1 from the opposite side as that shown in FIG. 2.
Figure 4:
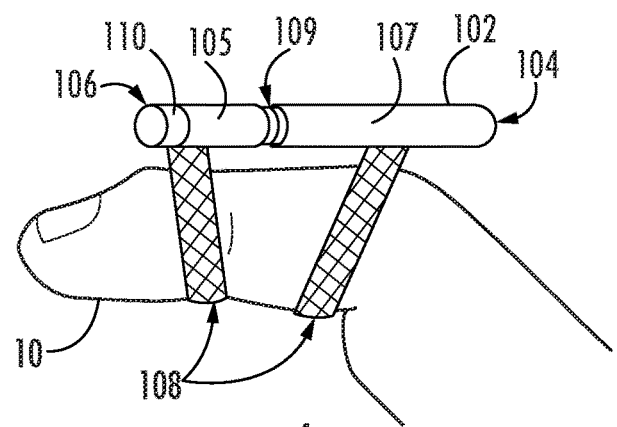
FIG. 4 illustrates a side view of the disposable thumb light of FIG. 1 attached to a finger of a user, in a state in which the light source is de-energized.
Figure 5:
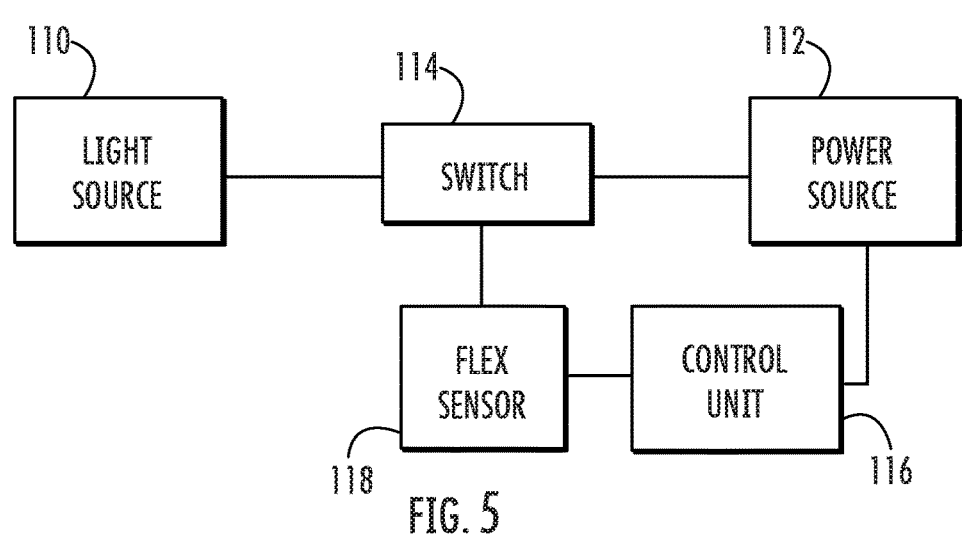
FIG. 5 illustrates a schematic diagram of the electrical components of the disposable thumb light of FIG. 1.

Referring now to FIG. 1, one embodiment of a light 100 of the present invention is shown. As illustrated, the light 100 includes a housing 102 extending from a proximal end 104, which may be configured to be positioned nearer to a proximal portion of a user's hand, e.g., nearer to the wrist, to a distal end 106, which may be configured to be positioned nearer to a distal portion of a user's hand, e.g., nearer to the fingertips. FIGS. 2-4 illustrate the light 100 coupled to a user's thumb 10 in such a configuration. The housing 102 includes a flexible hinge 109 positioned between the proximal end 104 and the distal end 106 of the housing 102. A first section 105 of the housing 102 extends from the distal end 106 to the flexible hinge 109, and a second section 107 of the housing 102 extends from the flexible hinge 109 to the proximal end 104.

The overall shape of the housing 102 of the finger light 100 is not particularly limited and can vary depending on which finger (e.g., thumb, pointer finger, middle finger, ring finger or pinky finger) that a user intends to attach the light 100 to for use in a particular procedure. In general, the housing 102 is configured to have dimensions that correspond generally to a user's thumb. For instance, the first portion 105 has a length L1 that can be shorter than or about equal to a length of a distal phalange 14 from a tip of the thumb 10 to the interphalangeal joint of the thumb 12, as shown in FIG. 2. For example, the length L1 of the first portion 105 can be shorter than or equal to a distance from a proximal edge of the fingernail 18 of the thumb 10 to the interphalangeal joint 12 such that the housing 102 does not rest on the fingernail 18 of the thumb 10 when it is coupled to the thumb 10. The length L1 can be in a range from about 10 millimeters to about 130 millimeters, such as from about 15 millimeters to about 120 millimeters; for example, from about 20 millimeters. Similarly, the second portion 107 has a length L2 that can be shorter than or equal to the length of a proximal phalange 16 from the interphalangeal joint 12 to a proximal joint of the thumb 10, as shown in FIG. 2, such that the proximal end 104 of the housing 102 does not extend nearer to the user's hand than the proximal phalange 16. The length L2 can be in a range from about 10 millimeters to about 155 millimeters, such as from about 20 millimeters to about 120 millimeters; for example, about 30 millimeters.

The flexible hinge 109 is configured to be positioned generally in alignment with the interphalangeal joint 12 of a user's thumb 10, as shown in FIGS. 2-3, to enable the housing 102 to bend when the interphalangeal joint 12 flexes and to maintain the housing 102 in place on the user's thumb 10. The inclusion of the flexible hinge 109, can improve comfort while wearing an apparatus at least during flexion of the interphalangeal joint because of the large flex angle of the interphalangeal joint 12. For instance, the flexibility of the device can prevent pressure between the thumb 10 and the apparatus at least at the interphalangeal joint 12 of the thumb during flex. In particular, the interphalangeal joint 12 of the thumb 10 has a greater angle of flexion, alpha ($\alpha$), than any other interphalangeal joint of any other finger. Such flexibility of the interphalangeal joint 12 of the thumb 10 enables opposition of the thumb 10 and enhanced gripping ability of the thumb 10, e.g., as shown in FIG. 6.

Figure 6:
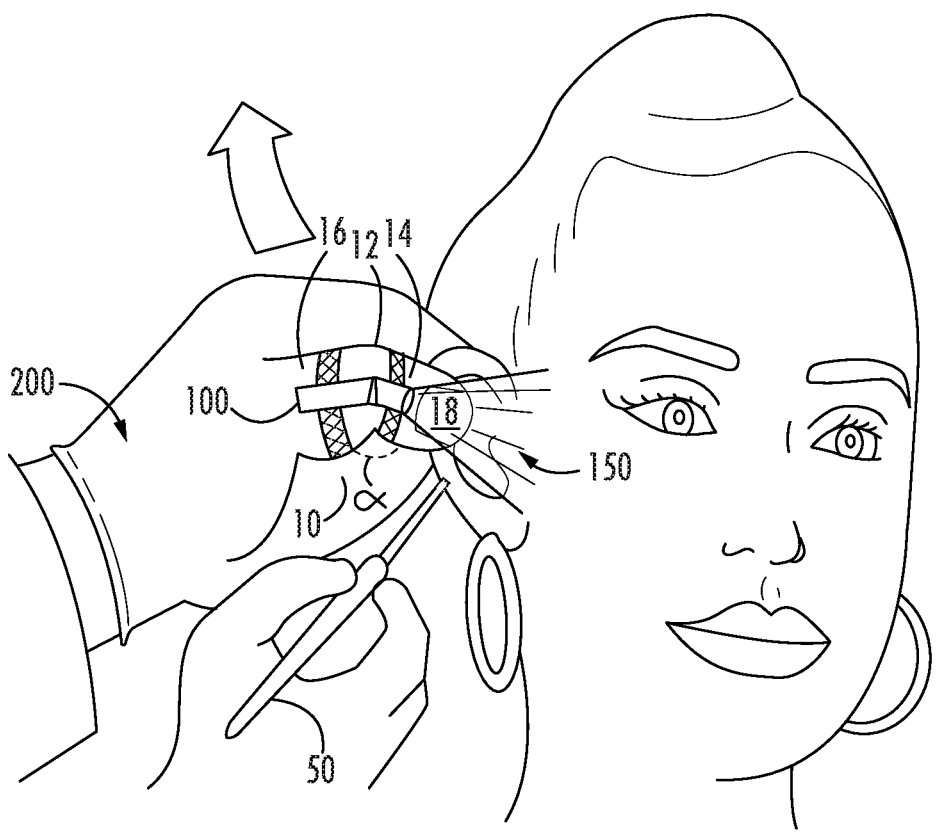
FIG. 6 illustrates a perspective view of the disposable thumb light of FIG. 1 in use in a method of providing direct lighting for a medical procedure on a patient.

In one embodiment, the housing 102 can have a width, or diameter D1, that can be less than or equal to a width or diameter of the user's thumb 10 in order to avoid increasing the profile of the user's thumb 10 in the width direction when the thumb light 100 is coupled to the thumb 10, thereby reducing the potential for the housing 102 to obstruct the movement of the user's thumb 10 during a procedure, e.g., as shown in FIG. 6. The diameter D1 can be in a range from about 5 millimeters to about 30 millimeters, such as from about 10 millimeters to about 25 millimeters; for example, from about 12 millimeters to about 20 millimeters.

As described above, the housing 102 can include a flexible hinge 109 disposed between the first portion 105 and the second portion 107. The flexible hinge 109 can be formed from a flexible polymer, an accordion-like angle-adjustable bellows segment, or other suitable flexible structure. The flexible hinge 109 enables the housing 102 to bend when the interphalangeal joint 12 bends when the housing 102 is coupled to the user's thumb 10. Thus, the housing 102 is configured to bend at the flexible hinge 109 when the interphalangeal joint 12 bends when the housing 102 is coupled to the user's thumb 10. When the flexible hinge 109 bends, the angle between the first portion 105 and the second portion 107 is changed. In general, the angle between the first portion 105 and the second portion 107 is approximately equal to the angle alpha ($\alpha$) of flexion of the interphalangeal joint 12 when the housing 102 is coupled to the thumb 10.

The housing 102 can be formed of any suitable medical grade material. In general, the housing 102 can be formed of a polymeric material (e.g., a molded polyethylene, polyvinyl chloride, polystyrene, or the like) that can be either disposable for single use applications or can be reusable and optionally sterilizable.

The housing 102 can further include at least one attachment 108, e.g., a plurality of attachments 108 as shown in FIGS. 1-2 and 4, in order to hold the housing 102 in place relative to the user's thumb 10. For instance, at least one attachment 108 can be on the first portion 105 of the housing 102 and at least one attachment 108 can be on the second portion 107 of the housing 102, such that at least one attachment 108 is disposed on either side of the flexible hinge 109. Each attachment may be, for example, a mating hook and loop fastener having a first attachment portion 120, e.g., a hook fastener, and a second attachment portion 122, e.g., a mating loop fastener. It is to be understood, however, that in some aspects of the invention, the first attachment portion 120 may be a loop fastener and the second attachment portion 122 may be a cooperating hook fastener, or that, when the housing 102 includes a plurality of attachments 108 in the form of hook and loop fasteners, the first and second portions 120 and 122 may each individually be selected as cooperating hook or loop fasteners, respectively.

Although the attachment(s) 108 are illustrated as cooperating hook and loop fasteners having a first attachment portion 120 and second attachment portion 122, other types of attachments may be used in the present invention to couple the housing 102 of the finger light 100 to a user's thumb 10 or glove, such as a medical exam glove or a non-medical glove. For instance, the at least one attachment 108 can be one or more of an adhesive, e.g., a releasable adhesive or a permanent adhesive, a clip, a clamp, a strap, a tie, or other attachment mechanism. For instance, an adhesive attachment may include one or more strips of fabric or plastic having adhesive material on one side of the strip similar to those of adhesive bandages commonly used to cover wounds by adhering to the skin. A clip attachment may include a pair of cooperating clip arms configured to surround a user's thumb 10 to hold the housing 102 in place relative to the user's finger 10.

The attachment(s) 108 are configured to be disposed on the housing 102 in a manner that is configured to align the flexible hinge 109 with the interphalangeal joint 12 of the user's thumb 10 when the disposable thumb light 100 is attached to the user's thumb 10 as shown in FIGS. 2-4 and 6. Thus, when the knuckle of the user's thumb 10 flexes at the interphalangeal joint 12, the flexible hinge 109 of the housing 102 is capable of bending along with the user's thumb 10. However, when the flexible hinge 109 is not aligned with the interphalangeal joint 12 of the user's thumb 10, the housing 102 may inhibit flexing of bending of the user's finger 10, which can result in undesired interference with a medical procedure being performed.

In an alternative embodiment, however, the housing 102 may be formed from a flexible or malleable material that is configured to bend or flex at any point along the length of the housing 102. In such an embodiment, any positioning of the housing 102 on the thumb 10 of the user is encompassed herein.

As shown in FIGS. 1-4 and 6, the disposable thumb light 100 includes a light source 110 disposed at the distal end 106 of the housing 102. The light source 110, when activated, illuminates an area 150 extending from the light source 110. For instance, when the finger light 100 is coupled to a user's thumb 10 as shown in FIGS. 2 and 3, the area 150 illuminated by the light source 110 is configured to extend beyond the tip of the user's thumb 10. The light source 110 can be any suitable type, and in one embodiment, can include at least one light emitting diode (LED). The housing 102 can include at least one transparent lens at the distal end 106 to enable the transmission of light out of the housing 102. In general, the light source 110 can be designed to emit white light; however, emission of light of one or more colors may be contemplated, either by a different LED and/or providing a cover at the distal tip 106 of the housing 102 over the light source 110.

In one embodiment, a light source 110 can deliver ultraviolet (UV) light to an area 150. UV light can be desirable in examination procedures in which a luminescent material is visualized. For instance, certain abnormal tissues can be visually detected by use of UV light. Diagnostic materials can also be detected by UV light. For instance, fluorescein solution can be applied to an area 150. Upon examination under UV light, tissue abnormalities can then be visually detectable. Such an embodiment can be used for the detection and/or visualization of tissues in a biopsy procedure. The finger light 100 can be used with cervical biopsy forceps, tissue biopsy forceps, and/or specimen biopsy forceps for any such biopsy procedure.

In another embodiment, the light source 110 can carry two different light emission devices, e.g., both a white LED emission source and a UV source. In this embodiment, the device can include electrical components, wires, switches, etc., examples of which are discussed further herein, that can allow the user to select which light emission is operating. Thus, during use the light emission in the area 150 can be modified as desired.

The thumb light 100 further includes related electronics necessary for the light source 110 to emit light from the distal end 106 of the housing 102 in an area 150. The housing 102 contains the light source 110 and one or more electrical components, e.g., electrical connections 111 such as wires, a switch 114, and power source 112 necessary for proper function of the light source 110. The switch 114 can be in electrical communication with the light source 110 and can be a single-use switch or a multi-use switch. For instance, in those embodiments in which the light 100 is a single-use, disposable device, the switch 114 can be a single-use switch, e.g., a tab formed of a non-conductive material. Upon removal of the tab, a circuit is closed between the power source 112 and the light source 110, and the light source 110 will be powered to emit light in the area 150. However, any switch type may alternatively be utilized including, without limitation, a slide switch, a toggle switch, a button switch, etc.

The light source 110 can be in electrical connection with power supply 112, such as one or more batteries 112. The battery 112 can be contained within the housing 102, such as within the handle portion 105 of the housing 102. The size and type of the power source 112, e.g., one or more batteries, can vary as is known, generally depending upon the load expected and whether the device is intended to be a single-use or multi-use device. For instance, the finger light 100 can include one or more 1.5V button-type batteries, e.g., disposable batteries, to power the light source 110.

Alternatively, a battery source external to the housing 102 can be operatively connected to the light source 110. For instance, a battery pack contoured to the fit the back of the hand and having an attachment or glove for the back of the hand can be provided. Similarly, a battery pack disposed in a housing that is configured to be affixed to a wearer's belt and having an electrical cable to connect to an electrical cable plug-in of the housing 102 can be provided as the power source 112.

In some aspects of the invention, the switch 114 can be a flex responsive switch. For instance, the switch 114 can be positioned proximate to or within the flexible hinge 109 of the housing 102 such that the switch 114 will be subject to flexure as the user's finger 10 is moved between an outstretched or straight position, and a bent position. Thus, placement of the switch 114 proximate to the flexible hinge 109 will subject the switch 114 to the desired flexure. For instance, the flex-responsive switch 114 can be configured to close and establish electrical communication between the power source 112 and the light source 110 to illuminate the light source 110 when the flexible hinge 109 is in a bent configuration, and then the flex-responsive switch 114 can be open when the flexible hinge 109 is in a straight or outstretched configuration to cease the electrical communication between the power source 112 and the light source 110. Thus, when the housing 102 is coupled to the user's thumb 10, the user can close and open the switch 114 merely by flexing the interphalangeal joint 12 of the thumb 10.

In some embodiments, the thumb light 100 can include a control unit 116 configured to sense or detect flexion in the flexible hinge 109 in order to control the power to the light source 110. For instance, the control unit 116 can include a flexion or strain sensor 118, e.g., a strain gauge, in operable communication with the flexible hinge 109 that is configured to detect flexure of the flexible hinge 109. The flexion or strain sensor 118 experiences a change in resistance due to a change in its shape in response to the flexion of the flexible hinge 109. The control unit 116 then detects the change in resistance of the flexion or strain sensor 118, and controls the power delivered to the light source 110 in response to the sensed resistance. For instance, the control unit 116 may selectively energize the light source 110 when the flexion or strain sensor 118 detects that the flexible hinge 109 is in a flexed or bent position and may selectively de-energize the light source 110 when the flexion or strain sensor 118 detects that the flexible hinge 109 is in a straight or outstretched position.

In general, when the user's thumb 10 is being used in a procedure, e.g., the thumb 10 is being used to manipulate a body part of a patient as illustrated in FIG. 6, the user's thumb 10 is in a bent state, i.e., the interphalangeal joint 12 is flexed at an angle α. When the thumb light 100 is coupled to the user's thumb 10, such bending or flexing of the user's thumb 10 would thus bend the housing 102 at the flexible hinge 109, as shown in FIG. 6. As such, if the flex-responsive switch 114 or control unit 116 is configured to energize the light source 110 when the flexible hinge 109 is bent, the light source 110 may be automatically energized when the user is using the finger 10 to perform a procedure.

In one embodiment, the angle α of the housing can be used to control the energizing of the light source. As discussed previously, the thumb 10 has a greater angle of flexion, alpha (α), than any other interphalangeal joint of any other finger, and this can be used to improve control of the light source. For instance, the light source can be designed such that it energizes at a predetermined angle α that is common for the interphalangeal joint of the thumb during ordinary grasping of the hand but that is greater than the angle of flexion of other interphalangeal joints of the hand. As such, a user can avoid energizing the light source other than at the desired time of examination. By way of example, the light source 110 can be energized upon bending of the flexible hinge 109 to an angle of about 45° or more; for instance, about 50° or more, such as from about 40° to about 100°, or about 90° in some embodiments.

The disposable thumb light 100 of the present invention is configured to be coupled to a user's thumb 10, e.g., onto an examination glove worn over a healthcare practitioner's hand for a procedure or other glove when used in a non-medical application. In particular, the size and shape of the housing 102 may be configured to be disposed on the thumb 10 of the user's hand. For instance, the dimensions of the housing may be particularly suited to the length between the tip of the thumb 10, the distal phalange 14, and the proximal phalange 16 of the thumb 10 such that the flexible hinge 109 aligns with the interphalangeal joint 12 of the thumb 10 when the attachment(s) 108 are secured to the thumb 10.

In another aspect of the invention, a glove 200 may be provided that incorporates the disposable thumb light 100 of the invention. The glove 200 may be a medical or a non-medical glove. For instance, a light source 110, switch 114, power source 112, and control unit 116 may be integrally incorporated into a glove 200, e.g., disposed on the thumb of the glove 200. In such an embodiment, the disposable thumb light 100 and glove 200 can be formed of a unitary construction, i.e., formed in one piece. In another aspect, the disposable thumb light 100 can be incorporated into the glove 200 by coupling the disposable thumb light 100 to the glove 200 prior to donning of the glove 200 by a user. For instance, an adhesive attachment may be used to couple the disposable thumb light 100 to the glove 200 to form an integrated glove-light assembly. When the glove 200 is a disposable, e.g. nitrile or latex, medical exam or procedure glove, the glove 200 and the disposable thumb light 100 may be disposed of together after completion of a medical examination or procedure using the glove-light assembly, without any need to uncouple the light 100 from the glove 200.

The disposable thumb light 100 of the present invention may be used in a method of providing direct lighting for a medical procedure on a patient. The method may include steps of providing the disposable thumb light 100 as described above; coupling the disposable thumb light to a thumb of the user; energizing the light source by moving the thumb of the user from a first position to a second position; and optionally, de-energizing the light source by moving the thumb of the user from the second position toward the first position. For instance, the flex sensor 118 may detect the movement of the thumb 10 from the first position to the second position and cause the switch 114 to energize the light source upon detection of the movement of the thumb 10 from the first position to the second position. Similarly, the flex sensor 118 may detect the movement of the thumb 10 from the second position to the first position and cause the switch 114 to de-energize the light source upon detection of the movement of the thumb 10 from the second position to the first position. In one possible arrangement, in the first position, the interphalangeal joint 12 of the thumb 10 is straight, and in the second position, the interphalangeal joint 12 of the thumb 10 is flexed. The step of energizing the light source 110 may cause the light source 110 to illuminate an area 150 extending from the light source 110 which extends beyond the fingertip of the thumb 10 of the user, e.g., as shown in FIGS. 3 and 6. For instance, the method may include a step of manipulating a patient's body part with the thumb 10 of the user in order to illuminate a target area of the patient's body coinciding with the area of illumination 150. In some aspects of the method, the disposable thumb light 100 is coupled to a thumb 10 of a manipulating hand of a user, and the method may further include a step of performing a medical procedure with the other hand of the user. For instance, as shown in FIG. 6, the left hand of the user is used to manipulate the patient's ear, including using the thumb 10 to grasp the patient's ear and illuminate an area 150 of the patient's ear and ear canal, while the right hand of the user is used to perform a procedure using a tool 50. While the thumb 10 of the manipulating hand is used to grasp the patient's body part, i.e., ear in FIG. 6, the flexion of the interphalangeal joint 12 necessary to grasp the ear causes the light source 110 to be energized to illuminate the area 150 including the patient's ear canal. Although FIG. 6 illustrates the left hand utilizing the thumb light 100 and the right hand performing a procedure using the tool 50, it is to be understood that the hand positioning can be reversed, i.e., the right hand may utilize the thumb light 100 and the left hand may perform a procedure.

Beneficially, through locating the light on the user's thumb, an improved field of view can be obtained, as the light from the light source 109 will be directed in a direction somewhat aligned with the inner wrist and forearm of the wearer, as illustrated in FIG. 6. This directional control of the light can better illuminate an area that is being grasped by the wearer as compared to a light that is held by a third party, which will be either behind the grasping hand (leading to shadowing by the grasping hand) or will direct the light across the surface being grasped, as well as compared to a light that is attached to another location on the grasping hand, e.g., on the wrist (in which case the wearer's hand can block the light) or on a finger (in which case the light would be directed across the surface being grasped).

Examples of medical procedures in which the disposable thumb light 100 of the present invention may be employed include: foreign body removal from a variety of body cavities; suturing; ear lavage; general physical examination of the body, e.g., the throat, mouth, eye, ear, and/or wounds; detecting gross lesions in the eye lids, sclera, and cornea; detecting pupillary abnormalities, i.e., anisocoria; estimating the anterior eye chamber depth in a patient suspected of acute angle closure glaucoma (increased intraocular pressure), by using an oblique flashlight test shining the light source 110 perpendicular to the visual axis of the eye.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A disposable thumb light comprising:
   a housing having a first portion, a second portion, and at least one flexible portion disposed between the first portion and the second portion, wherein the first portion is configured to be coupled to a thumb distal to the interphalangeal joint, and wherein the second portion is configured to be coupled to the thumb proximal to the interphalangeal joint;
   a light source; and
   at least one attachment configured to couple the disposable thumb light to a thumb of a user or a glove, the at least one attachment comprises one or more of an adhesive attachment, a clip, a magnet, a hook and loop fastener, a tie, or a combination thereof, wherein the at least one attachment is configured to be attached around at least a portion of the user's thumb or the glove.

2. The disposable thumb light of claim 1, further comprising a switch in electrical communication with the light source.

3. The disposable thumb light of claim 2, wherein the switch is a flex responsive circuit comprising a flex responsive switch, wherein the flex responsive switch is configured to move between at least a first position and a second position when the housing moves from a first housing position to a second housing position.

4. The disposable thumb light of claim 3, wherein the flex responsive circuit is configured to measure the amount of flexion to detect when the housing moves from a first position having a bend angle at the flexible portion in a range from about 0° to about 40°, to a second position having a bend angle at the flexible portion greater than 40°.

5. The disposable thumb light of claim 1, wherein the housing is flexible between at least a first position and a second position.

6. The disposable thumb light of claim 1, wherein the at least one attachment comprises a first attachment coupled to the first portion of the housing and a second attachment coupled to the second portion of the housing.

7. The disposable thumb light of claim 1, wherein the first portion is adapted to be shorter than a distance between a proximal edge of a fingernail of the thumb to an interphalangeal joint of the thumb.

\* \* \* \* \*